United States Patent [19]

Uzan

[11] 4,263,303
[45] Apr. 21, 1981

[54] ANALGESIC COMPOSITION
[75] Inventor: Andre V. Uzan, Paris, France
[73] Assignee: Pharmindustrie, Gennevilliers, France
[21] Appl. No.: 56,753
[22] Filed: Jul. 12, 1979
[30] Foreign Application Priority Data
Jul. 13, 1978 [FR] France .................. 78 20969
[51] Int. Cl.³ .................. A61K 31/445; A61K 31/485
[52] U.S. Cl. .................. 424/260; 424/267
[58] Field of Search .................. 424/260, 267
[56] References Cited
U.S. PATENT DOCUMENTS
4,064,255  12/1977  Champseix et al. .................. 424/267

OTHER PUBLICATIONS
Chem. Abst, 83—188,234V (1975).

Primary Examiner—Stanley J. Friedman
Attorney, Agent, or Firm—Beveridge, DeGrandi, Kline & Lunsford

[57] ABSTRACT

A novel analgesic composition which comprises a compound of Formula (I):

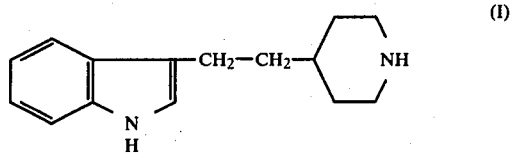

and morphine or a morphine derivative and a method of treating a mammal afflicted with hyperalgesia therewith.

4 Claims, No Drawings

ANALGESIC COMPOSITION

The invention relates to an analgesic composition that is effective during treatment of hyperalgesia.

Present therapy for hyperalgesia rests on two types of products. Some, comprising non-steroid anti-inflammatories, owe their activity to essentially peripheral effects. Others, comprising the opiate group and particularly morphine, owe their activity to a purely central effect.

Recent advances made in the knowledge of the action machanism of morphine analgesics have shown the intervention of neuromediators having a peptide structure and of pain-controlling central neuronal receptors. These recent data, however, do not rule out the well-established role of serotonin-dependent contral tryptaminergic regulations in the modulation of hyperalgia or analgesia.

These two mechanisms under consideration are not opposed to one another but rather seem to be complementary.

The role of serotonin (5-HT) in sensitivity to painful stimuli is widely accepted. Thus, for example, central lesions of the tryptaminergic neurons or 5-HT depletion cause an increase in the painful response to electric stimulus (Harvey, J. A. et al., Sciences, 148, 250, (1965)).

In the light of these bibliographic data it appears that the administration of a proserotoninergic substance, during analgesic treatment with morphine or morphine derivative, is able to improve its effects.

Such a synergy seems particularly desirable because it could take the place of morphine treatments or reduce these treatments in posology and duration by a potentiation effect.

Knowing the undesirable effects that opiates cause and the risks of habituation which they run, the interest in an alternative or in synergy is quite obvious. However, few substances are really able to intensify the neuronal functions of cerebral 5-HT.

The precursors of 5-HT such as 5-HTP or tryptophan must be administered in very high doses and despite this their effectiveness is debatable and their secondary effects are not inconsiderable.

The recapture inhibitors of 5-HT are therefore a priori able to show appreciable proserotoninergic properties. However, so far, their activity and their specificity have been insufficient, which would explain the absence of analgesic activity and the absence of synergy. of chlorimipramine with morphine. In the case of this substance of the tricyclic group, still the most specific of this group in regard to 5-HT, the effectiveness can be explained by its transformation, in the organism, into chlordesipramine whose activity bears mainly on the inhibition of noradrenalin uptake.

It has now been found, according to the present invention, that a composition comprising morphine or a morphine derivative such as pethidine and a very specific and very active inhibitor of neuronal and platelet uptake of serotonin of Formula (I) exhibits very strong analgesic properties

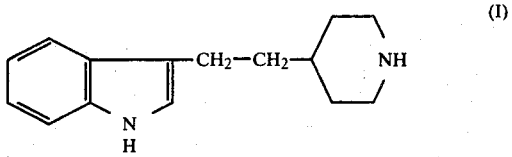

Depending on the nature and type of the morphine derivative used, the proportion by weight of the morphine derivative in the composition varies from 0.1 to 10 times the weight of the compound of Formula (I) as preferred ranges. Thus, in the case of morphine, this proportion by weight varies from 0.25 to 0.5 times the weight of the compound of Formula (I) and in the case of pethidine it varies from 1 to 2 times the weight of the compound of Formula (I).

The analgesic activity of morphine is potentiated by the compound of Formula (I) whereas chlorimipramine, another inhibitor of 5-HT uptake, does not do so.

Therefore, it can be considered that the compound of Formula (I) benefits from these properties undoubtedly as a powerful and specific inhibitor of 5-HT uptake (Le Fur et al., Biochem. Pharmacol. 26, 497, 1977) but it can also be, thanks to a particular regional cerebral effect, at the level of certain receptors.

The compound of Formula (I) is known and is described particularly in U.S. Pat. No. 4,064,255.

Pharmacological Properties

Potentiation of the analgesic activity of morphine by the compound of Formula (I) was shown experimentally with rats and mice by measurement of the antinociceptive reflex caused in the animal when placed on a hot plate.

Study With Rats

The method used was that of Sugrue et al. [J. Pharm. Pharmacol., 28, 447, (1976)].
Experimental procedure:
Male rats (lots of 8 animals) from Charles River stock, weighing 70 to 90 g, received an intraperitoneal (IP) injection either of the compound of Formula (I) (20 mg/kg) or of 5-HTP (150 mg/kg) of chlorimipramine (20 mg/kg) of physiological serum for the controls. Thirty minutes later, they received a second injection, either of morphine (subcutaneously, 4 mg/kg) or of physiological serum. After thirty minutes, each rat was individually placed on a plate heated to 55° C. The appearance time of the antinociceptive reflex was then noted. The maximum exposure time was 60 seconds. The results obtained are shown in the following Table I.

They show that under the test conditions described the compound of Formula (I), 5-HTP and chlorimipramine do not exhibit their own analgesic effect on rats.

However, the compound of Formula (I) potentiates significantly the analgesic activity of morphine by substantially doubling the appearance time of the antinociceptive reflex in reaction to animals receiving only morphine.

Chlorimipramine and 5-HTP result in increases not significantly different from those given by morphine alone.

Study With Mice

The method used was that of Jacob et al. [Arch. Int. Pharmacodyn., 133, 296, (1961)].

Experimental procedure:

Male mice (Charles River stock) weighing 24 to 28 g (lots of 8 animals) received an intraperitoneal injection either of the compound of Formula (I) (20 mg/kg) or of comparison products: 5-HTP (150 to 200 mg/kg), chlorimipramine, desipramine (20 mg/kg) or a physiological serum for the controls. After thirty minutes, the animals received an injection of morphine (subcutaneously (SC) 8 mg/kg), or nalorphine (intraperitoneally (IP) 50 mg/kg) or physiological serum. After thirty minutes, each mouse was placed on a plate heated to 65° C. The appearance time of the antinociceptive reflex was noted. Three successive exposures on the hot plate were made, the maximum time of each exposure being 60 seconds. The results are given in the following Table II.

It was found that in each test morphine extends to a considerable extent the appearance time of the reflex, this effect being maximal during the 3rd exposure on the hot plate.

Nalorphine is without effect, as could be expected.

The compound of Formula (I) and 5-HTP have their own slight analgesic action on mice at a dose of 20 mg/kg (intraperitoneally). Chlorimipramine and desipramine are without effect.

Nalorphine is antagonistic to the action of the compound of Formula (I) and 5-HTP, since, when they are associated with this product, their own slight effect is no longer noted.

On the other hand, the compound of Formula (I) and 5-HTP potentiate very clearly the analgesic action of morphine both during the 1st and 2nd and especially the 3rd exposure.

Chlorimipramine does not modify the activity of morphine under the same conditions.

The potentiation of morphine by the compound of Formula (I) is very important since, at the 3rd exposure, the appearance time of the antinociceptive reflex of the mouse, which had already been quadrupled by morphine alone, was prolonged still more by association with the compound of Formula (I), the times in this case being 5 to 10 times greater than those of the controls.

TABLE I

| | Analgesic Activity in Rats | | | |
|---|---|---|---|---|
| PRODUCT | DOSE mg/kg | ROUTE | Appearance Time In Seconds In Relation To Controls Of The Pain Threshold | |
| Controls | — | | | |
| Morphine | 4 | SC | 37.5 | ++ |
| 5-HTP | 150 | IP | 9.9 | NS |
| Compound of Formula (I) | 20 | IP | 9.5 | NS |
| Chlorimipramine | 20 | IP | 13.5 | NS |
| Morphine + 5-HTP | 4 150 | SC IP | 41.2 | NS |
| Morphine + Compound of Formula (I) | 4 20 | SC IP | 58.9 | ++ |
| Morphine + Chlorimipramine | 4 20 | SC IP | 51.2 | NS |

++ = 0.001<p<0.01
NS = not significant

TABLE II

| | Analgesic Activity in Mice | | | | |
|---|---|---|---|---|---|
| PRODUCT | ROUTE | DOSE mg/kg | Appearance Time In Seconds of Antinociceptive Reflex | | |
| | | | 1st exposure | 2d exposure | 3d exposure |
| Controls | — | — | 4.7–6.5 | 6.6–7.6 | 3.5–5 |
| Morphine | SC | 8 | 15.7 | 16.5 | 20 |
| Nalorphine | IP | 50 | 7.9 | 6.6 | 3.9 |
| 5-HTP | IP | 150 | 11.2 | 19.5 | 12.4 |
| | | 200 | 11.5 | 10.9 | 5.8 |
| Chlorimipramine | IP | 20 | 7.5 | 6.5 | 3.1 |
| Desipramine | IP | 20 | 7 | 8.7 | 7 |
| Compound of Formula (I) | IP | 20 | 8.7–10.4 | 10–13.2 | 5.7–5.9 |
| Morphine + Chlorimipramine | SC IP | 8 20 | 11.2 | 11.9 | 12.6 |
| Morphine + 5-HTP | SC IP | 8 200 | 42.5 | 51 | 54.4 |
| Morphine + Desipramine | SC IP | 8 20 | 9 | 13.3 | 12.7 |
| Morphine + Compound of Formula (I) | SC IP | 8 20 | 31.6 | 40 | 48.7 |
| Nalorphine + Compound of Formula (I) | IP IP | 50 20 | 9.2 | 6.9 | 6.1 |
| Nalorphine + 5-HTP | IP IP | 50 150 | 5.4 | 3.6 | 4.1 |

The analgesic effect of the composition according to the present invention was shown experimentally in mice.

Experimental procedure:

Mice CD1, weighing 25 to 29 g received the composition according to the present invention either subcutaneously or intraperitoneally depending on the morphine derivative used. After thirty minutes, they underwent a test on a hot plate brought to 65° C. according to Barthelemy et al. [J. Pharmacol. (Paris), 2, 35, (1971)] (three successive exposures at 5 minute intervals, maximum exposure time 60 seconds). The appearance time of the antinociceptive reflex was noted (simultaneously of the front paws, jump or adjusted leap). The results are shown in Table III which shows that the compound of Formula (I), administered at the same time as the morphine or pethidine, potentiates the analgesic effect of these two products.

With the doses used, 30 mg/kg subcutaneously and 20 mg/kg intraperitoneally, the compound of Formula (I) causes a very slight and insignificant effect.

Morphine, at 8 mg/kg subcutaneously, causes an effect significantly different from the controls during the three exposures. The analgesia is considerable at the 3rd exposure, which corresponds to an effect specific to morphine according to Barthelemy et al. The morphine effect is potentiated in the composition and the activity is particularly important and significant at the 3rd exposure.

TABLE III
Analgesic Activity of the Composition in Mice

| Products | DOSE mg/kg Route | Appearance Time of Antinociceptive Reflex in Seconds 1st Exposure | | | | |
|---|---|---|---|---|---|---|
| | | Average S ± SE | Difference in Relation to Controls P | Effect (%) | Difference in Relation to the Analgesic P | Effect (%) |
| Control | Sol. 9% NaCl IP | 5.7 ± 1.2 | — | — | — | — |
| Morphine | 8 SC | 13.2 ± 2.8 | 0.05 | 234 | — | — |
| Compound of Formula (I) | 30 SC | 8.9 ± 2.3 | NS | 154 | — | — |
| Morphine + Compound of Formula (I) | 8 SC 30 SC | 24.1 ± 7.1 | 0.05 | 419 | 0.20 | 182 |
| Pethidine | 40 IP | 9.5 ± 1.1 | 0.10 | 160 | — | — |
| Compound of Formula (I) | 20 IP | 7.6 ± 0.9 | NS | 132 | — | — |
| Pethidine + Compound of Formula (I) | 40 IP 20 IP | 30.8 ± 8.6 | 0.02 | 535 | 0.05 | 332 |

| Products | DOSE mg/kg Route | Appearance Time of Antinociceptive Reflex in Seconds 2nd Exposure | | | | |
|---|---|---|---|---|---|---|
| | | Average S ± SE | Difference in Relation to Controls P | Effect (%) | Difference in Relation to the Analgesic P | Effect (%) |
| Control | Sol. 9% NaCl IP | 6.8 ± 1.1 | — | — | — | — |
| Morphine | 8 SC | 11.2 ± 1.2 | 0.02 | 164 | — | — |
| Compound of Formula (I) | 30 SC | 8.7 ± 1.6 | NS | 127 | — | — |
| Morphine + Compound of Formula (I) | 8 SC 30 SC | 34.7 ± 9.2 | 0.01 | 510 | 0.05 | 308 |
| Pethidine | 40 IP | 12.7 ± 3.9 | 0.20 | 186 | — | — |
| Compound of Formula (I) | 20 IP | 8.5 ± 2.2 | NS | 125 | — | — |
| Pethidine + Compound of Formula (I) | 40 IP 20 IP | 23.6 ± 8.1 | 0.10 | 347 | NS | 185 |

| Products | DOSE mg/kg Route | Appearance Time of Antinociceptive Reflex in Seconds 3rd Exposure | | | | |
|---|---|---|---|---|---|---|
| | | Average S ± SE | Difference in Relation to Controls P | Effect (%) | Difference in Relation to the Analgesic P | Effect (%) |
| Control | Sol. 9% NaCl IP | 4.1 ± 0.8 | — | — | — | — |

TABLE III-continued
Analgesic Activity of the Composition in Mice

| | | | | | | |
|---|---|---|---|---|---|---|
| Morphine | 8 SC | 11 ± 1.8 | 0.01 | 268 | — | — |
| Compound of Formula (I) | 30 SC | 9.2 ± 3.2 | NS | 224 | — | — |
| Morphine + Compound of Formula (I) | 8 SC 30 SC | 37.1 ± 7.8 | 0.001 | 904 | 0.01 | 337 |
| Pethidine | 40 IP | 5.1 ± 0.4 | NS | 124 | — | — |
| Compound of Formula (I) | 20 IP | 6.5 ± 0.7 | 0.10 | 158 | — | — |
| Pethidine + Compound of Formula (I) | 40 IP 20 IP | 23 ± 8.2 | 0.05 | 560 | 0.05 | 449 |

S = Time in Seconds
SE = Type variation
P = Probability according to test t of Student.

The dose of 40 mg/kg intraperitoneally of pethidine was found to be mildly analgesic and only slightly significant. Association of the compound of Formula (I) caused the expected effect of the pethidine to appear. While at the 2nd exposure the potentiating effect was insignificant, the 3rd exposure, on the other hand, showed a strong potentiation. This association therefore acted in the same way as the association with morphine.

In conclusion, these results show that the compound of Formula (I), associated with morphine or pethidine, potentiates or brings out the analgesic effect of the two narcotics studied.

Toxicological Properties

Administration of the association of morphine derivative and compound of Formula (I) did not show manifestation of any nature in comparison, on the one hand, with administration of the two constituents taken separately and, on the other hand, with the administration of morphine with other 5-HT uptake inhibiting substances of a different chemical structure such as chlorimipramine.

Therapeutic Use

The composition according to the present invention can be used in mammalian, including but not limited to human, therapy in the form of injectable or ingestible aqueous solutions, suppositories, pills, tablets, lozenges, troches, capsules and the like for treatment of hyperalgesia.

The daily posology can be a composition containing between 0.0025 mg/kg and 125 mg/kg of morphine derivative and between 0.01 mg/kg and 500 mg/kg of the compound of Formula (I).

Examples of Pharmaceutical Formulations

Injectable aqueous solutions

| Formulation 1: | |
|---|---|
| Morphine hydrochloride | 10 mg |
| Compound of Formula (I) | 10 mg |
| Ascorbic acid | 12 mg |
| Sodium metabisulfite | 10 mg |
| Sodium chloride | 10 mg |
| Sufficient water for injectable preparation | 2 ml |
| Formulation 2: | |
| Morphine hydrochloride | 20 mg |
| Compound of Formula (I) | 50 mg |
| Ascorbic Acid | 60 mg |
| Sodium metabisulfite | 25 mg |
| Sodium chloride | 10 mg |
| Sufficient water for injectable preparation | 5 ml |

| Formulation 3: | |
|---|---|
| Pethidine hydrochloride | 10 mg |
| Compound of Formula (I) | 10 mg |
| Ascorbic acid | 12 mg |
| Sodium metabisulfite | 10 mg |
| Sodium chloride | 10 mg |
| Sufficient water for injectable preparation | 2 ml |
| Formulation 4: | |
| Pethidine hydrochloride | 50 mg |
| Compound of Formula (I) | 50 mg |
| Ascorbic acid | 60 mg |
| Sodium metabisulfite | 25 mg |
| Sodium chloride | 10 mg |
| Sufficient water for injectable preparation | 5 ml |
| Formulation 5: | |
| Pethidine hydrochloride | 100 mg |
| Compound of Formula (I) | 100 mg |
| Ascorbic acid | 120 mg |
| Sodium metabisulfite | 50 mg |
| Sodium chloride | 20 mg |
| Sufficient water for injectable preparation | 10 ml |

The process for preparing these 5 formulations of injectable aqueous solutions is as follows:

The constituents are dissolved in water degased by being boiled and cooled or by bubbling nitrogen. The solution is divided into ampoules under a nitrogen atmosphere, and the ampoules are sterilized at 100° C. for one hour in an autoclave.

The aqueous solutions can be sterilized by filtering and sterile distribution. The ampoules are to be kept away from light.

Suppositories

| Formulation 1: | |
|---|---|
| Pethidine hydrochloride | 10 mg |
| Compound of Formula (I) | 10 mg |
| Butylhydroxyanisol | 2 mg |
| Sufficient semi-synthetic glyceride | 2 g |
| Formulation 2: | |
| Pethidine hydrochloride | 50 mg |
| Compound of Formula (I) | 25 mg |
| Butylhydroxyanisol | 2 mg |
| Sufficient semi-synthetic glyceride | 2 g |
| Formulation 3: | |
| Pethidine hydrochloride | 100 mg |
| Compound of Formula (I) | 50 mg |
| Butylhydroxyanisol | 2 mg |
| Sufficient semi-synthetic glyceride | 2 g |
| Formulation 4: | |
| Pethidine hydrochloride | 100 mg |
| Compound of Formula (I) | 100 mg |
| Butylhydroxyanisol | 2 mg |
| Sufficient semi-synthetic glyceride | 2 g |

The process of preparing these 4 suppository formulas is as follows:

BHA (butylhydroxyanisol) is dissolved in the molten excipient mass. The pethidine hydrochloride is added and then the compound of Formula (I) with mixing. The mixture is homogenized with a colloidal mill or shearing homogenizer and poured into 2-gram molds and cooled.

Where appropriate, the entire remaining disclosure under the heading THERAPEUTIC APPLICATIONS in cols. 9 and 10 of U.S. Pat. No. 4,064,255 are incorporated herein by reference.

What is claimed is:

1. An analgesic composition which comprises a compound of formula (I):

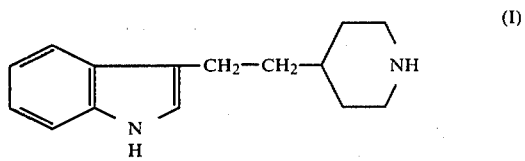

and morphine or pethidine wherein the proportion by weight of morphine or pethidine varies from 0.1 to 10 times the weight of the compound of formula (I).

2. Analgesic composition according to claim 1 wherein the proportion of weight of morphine varies from 0.25 to 0.5 times the weight of the compound of formula (I).

3. Analgesic composition according to claim 1 wherein the proprotion by weight of pethidine varies from 1 to 2 times the weight of the compound of formula (I).

4. A method of treating a mammal afflicted with hyperalgesia which comprises administering to said mammal a therapeutically effective amount of the composition of claim 1 in a pharmaceutically acceptable carrier therefor.

* * * * *